United States Patent [19]

Martinez et al.

[11] Patent Number: 4,766,127

[45] Date of Patent: Aug. 23, 1988

[54] 2-(3-PYRIDYLMETHYL)NAPHTHALENE-6-CARBOXYLIC ACID AS A THROMBOXANE SYNTHETASE INHIBITOR

[75] Inventors: Gregory R. Martinez, Palo Alto; John J. Bruno, Redwood City, both of Calif.

[73] Assignee: Syntex (U.S.A.) Inc., Palo Alto, Calif.

[21] Appl. No.: 12,979

[22] Filed: Feb. 10, 1987

[51] Int. Cl.$^4$ .................. A61K 31/435; C07D 213/06
[52] U.S. Cl. ..................................... 514/277; 546/342
[58] Field of Search ........................ 546/342; 514/277

[56] References Cited

U.S. PATENT DOCUMENTS 4,590,200  5/1986  Cross et al. .................. 546/342

Primary Examiner—Mary C. Lee
Assistant Examiner—Zinna Northington
Attorney, Agent, or Firm—Brian Lewis; Tom Moran

[57] ABSTRACT

The invention concerns a method of inhibiting thromboxane synthetase with a compound of the formula:

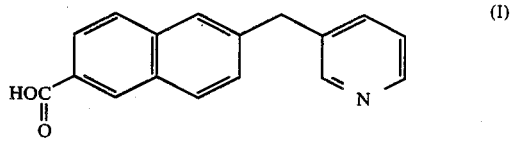

or a pharmaceutically acceptable salt or ester thereof, in a mammal having a disease characterized by elevated thromboxane levels or an imbalance of prostacyclin-thromboxane levels.

3 Claims, No Drawings

2-(3-PYRIDYLMETHYL)NAPHTHALENE-6-CARBOXYLIC ACID AS A THROMBOXANE SYNTHETASE INHIBITOR

BACKGROUND OF THE INVENTION

1. Field of the Invention

This invention concerns 2-(3-pyridylmethyl)naphthalene-6-carboxylic acid as an inhibitor of thromboxane synthetase activity and its use as an agent in the treatment of diseases characterized by an overproduction of thromboxane or an imbalance of thromboxane/prostacyclin.

2. Related Disclosures

Research work has established that in many tissues the major product of arachidonic acid metabolism by the cyclooxygenase enzyme system is either of two unstable substances, thromboxane $A_2$ (TxA$_2$) or prostacyclin (PGI$_2$). The discovery of TxA$_2$ and PGI$_2$ has significantly increased our understanding of vascular homeostasis. PGI$_2$ for instance is a powerful vasodilator and inhibitor of platelet aggregation, and in this last respect is the most potent endogenous substance so far discovered. The PGI$_2$ synthetase enzyme is located in the endothelial layer of the vasculature, and while it has its own cyclooxygenase system it can utilize endoperoxides released by blood platelets when thromboxane synthetase is inhibited.

TxA$_2$ is synthesized by the thromboxane synthetase enzyme which is located in, for example, the blood platelets. TxA$_2$ is a powerful vasoconstrictor and proaggregatory substance, the direct opposite functions to those of PGI$_2$. A balance in favor of PGI$_2$ is regarded as beneficial in many conditions such as thrombosis, atherosclerosis, vasospastic cardiovascular disease, diabetes, renal disorders, inflammation, endotoxic shock and possibly even tumor metastasis.

The foregoing demonstrates the desirability of altering the prostacyclin/thromboxane ratio in favor of the former. One method of attempting to achieve this goal is to take advantage of the fact that the immediate precursor to both PGI$_2$ and TxA$_2$ is the same substance, the unstable endoperoxide PGH$_2$. If the synthesis of TxA$_2$ can be blocked, it is then reasonable to expect that more PGH$_2$ will be available for conversion to PGI$_2$. This activity has been demonstrated by several compounds, e.g., dazoxiben, but the levels of prostacyclin thus produced are quite low and may not be therapeutically useful.

Certain 2-(3-pyridylmethyl)naphthalene-6-carboxylic acids and 2-(3-pyridylmethyl)naphthalene-7-carboxylic acids are broadly disclosed in U.S. Pat. No. 4,590,200 to Cross et al. as thromboxane synthetase inhibitors. Of the large family of compounds disclosed, 2-(3-pyridylmethyl)-naphthalene-7-carboxylic acids are indicated as preferred compounds. In particular, 1-methyl-2-(3-pyridylmethyl)-naphthalene-7-carboxylic acid is shown as one of nine most preferred compounds. Surprisingly, we have now discovered that 2-(3-pyridylmethyl)-naphthalene-6-carboxylic acid has unexpectedly greater activity as a thromboxane synthetase inhibitor than 2-(3-pyridylmethyl)-naphthalene-7-carboxylic acid by a factor of about 200.

SUMMARY OF THE INVENTION

One aspect of the invention concerns a method of inhibiting thromboxane synthetase in a mammal, particularly a human, having a disease characterized by elevated thromboxane levels or an imbalance of prostacyclin/thromboxane levels which method comprises:

administering to a mammal in need of such a treatment a therapeutically effective amount of a compound of the formula

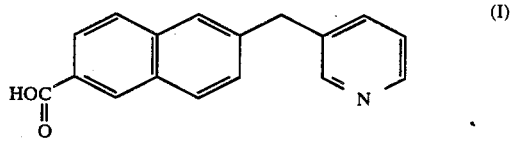

or a pharmaceutically acceptable salt or ester thereof.

In another aspect, the invention concerns a pharmaceutical composition containing a therapeutically effective amount of a compound of formula I admixed with at least one pharmaceutically acceptable excipient.

Yet another aspect of the invention concerns a compound of the formula

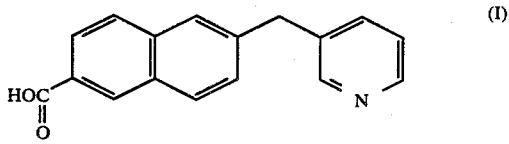

or a pharmaceutically acceptable salt or ester thereof.

Finally, the invention relates to a novel process for preparing the compound of Formula I.

DETAILED DESCRIPTION OF THE INVENTION

Definitions

The compound of the invention herein may be converted to a salt or an ester by virtue of the presence of a carboxylic acid group. "Pharmaceutically acceptable non-toxic salts and esters" refers to those salts and esters which retain the biological effectiveness and properties of the corresponding free acid and which are not biologically or otherwise undesirable. The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, distillation or a combination of these procedures. Specific illustrations are described in the Examples. However, other equivalent separation or purification procedures can be used.

The salt products are also isolated by conventional means. For example, the reaction mixtures can be evaporated to dryness and the salts then further purified by standard methods such as those listed above.

METHODS OF PREPARATION

The preparation of the compound of Formula (I) is illustrated in the Reaction Scheme below.

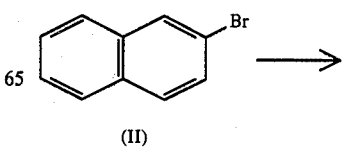

(II)

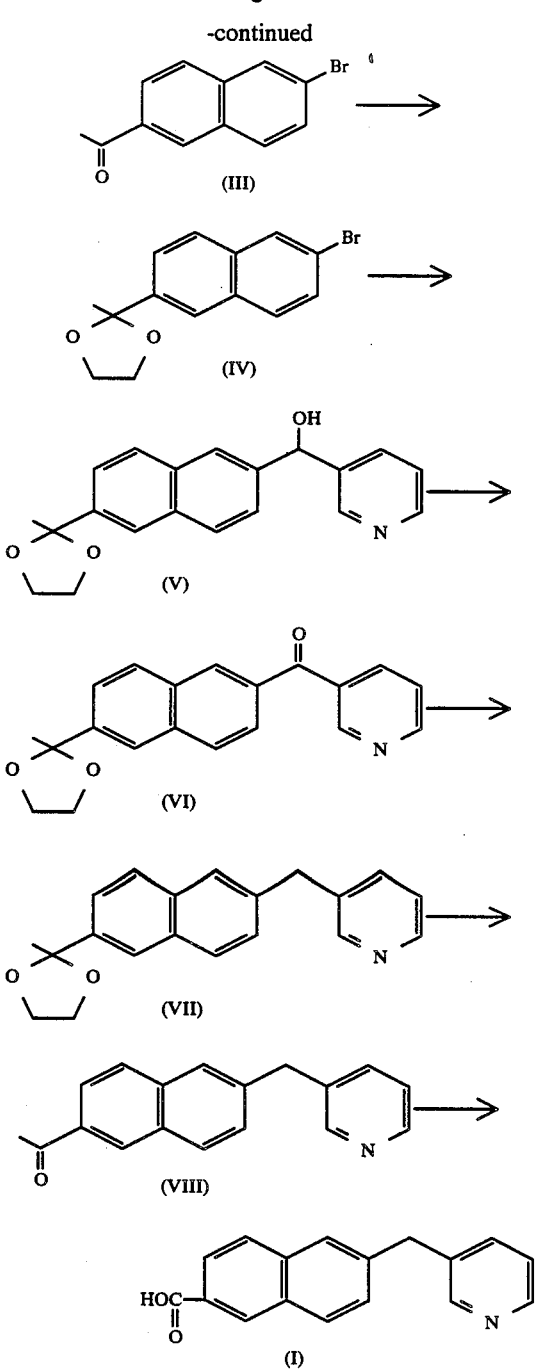

formula (III) is isolated by conventional means, for example crystallization.

The compound of formula (III) is then reacted with ethylene glycol to form a ketal, the compound of formula (IV). The reaction is carried out in an aromatic hydrocarbon solvent, for example xylene, toluene or preferably benzene, at reflux temperature in the presence of an acid catalyst such as hydrochloric acid, methanesulfonic acid or preferably p-toluenesulfonic acid, removing water as it is formed. When the reaction is substantially complete, the product of formula (IV), 2-bromo-6-(2-methyl-1,3-dioxolan-2-yl)naphthalene, is isolated by conventional means, for example crystallization.

The compound of formula (IV) is then reacted with an alkyl lithium, preferably t-butyl lithium, to form an anion. Typically, the compound of formula (IV) is dissolved in an ethereal solvent, preferably tetrahydrofuran, and cooled to 31 78° C. About 2 molar equivalents of t-butyl lithium are then added dropwise and the mixture is stirred for about 30 minutes to 5 hours, preferably about 1.5 hours. About 1 molar equivalent of 3-pyridine carboxaldehyde in tetrahydrofuran is then slowly added and the mixture allowed to warm to about −20° C. over a period of about 30 minutes. When the reaction is substantially complete, the product of formula (V), 2-[(3-pyridyl)hydroxymethyl]-6-(2-methyl-1,3-dioxolan-2-yl)naphthalene, is isolated by conventional means, for example crystallization.

The compound of formula (V) is then oxidized to the compound of formula (VI) with, for example, a solution of chromic acid in sulfuric acid (Jones reagent), sodium dichromate, an organic chromium reagent, for example pyridinium chlorochromate, or preferably oxalyl chloride and dimethylsulfoxide. Typically, oxalyl chloride is dissolved in an inert solvent, preferably methylene chloride, and cooled to about −40° C. to −80° C., preferably about −50° C. About 2 molar equivalents of dimethyl sulfoxide in methylene chloride is then added dropwise and the mixture stirred for about 5 minutes. About 1 molar equivalent of the alcohol of formula (V) in methylene chloride is then added dropwise and the mixture stirred at about −50° C. for about 15 minutes. About 5 molar equivalents of a tertiary organic base is then added, preferably triethylamine, at about −50° C. and the mixture stirred for about 5 minutes than allowed to warm to room temperature. When the reaction is substantially complete, the product of formula (VI), 2-(3-pyridylcarbonyl)-6-(2-methyl-1,3-dioxolan-2-yl)naphthalene, is isolated by conventional means, for example crystallization.

The compound of formula (VI) is then reduced to the compound of formula (VII), preferably with hydrazine. The reaction is carried out by reacting the compound of formula (VII) with a large excess, for example about 50 molar equivalents, of anhydrous hydrazine and about 10 molar equivalents of potassium hydroxide in a high boiling protic solvent, for example triethylene glycol. The reaction is initially conducted at a temperature of about 120° C. to 200° C., preferably about 150° C., for about 30 minutes. The reaction temperature is then raised to about 180° C. to 250° C., preferably about 210° C., for about 1-6 hours, preferably about 2 hours. When the reaction is substantially complete, the product of formula (VII), 2-(3-pyridylmethyl)-6-(2-methyl-1,3-dioxolan-2-yl)naphthalene, is isolated by conventional means, for example chromatography.

The compound of formula (II), 2-bromonaphthalene, is reacted with about 1 to 4 molar equivalents, preferably about 1.5 molar equivalents, of an acetyl halide, preferably acetyl chloride, in the presence of about 0.1 to 15 molar equivalents, preferably about 5 to 7 molar equivalents, of a Friedel-Crafts catalyst such as ferric chloride, zinc dichloride, tin tetrachloride, boron trifluoride or preferably aluminum trichloride, in a suitable solvent such as nitromethane, carbon disulphide, acetonitrile, methylene chloride or preferably nitrobenzene. The reaction is conducted at a temperature of about 25°–100° C., preferably about 50° C., for about 1-24 hours, preferably about 4 hours, giving the compound of formula (III), 2-bromo-6-acetylnaphthalene. When the reaction is substantially complete, the product of Alternatively, the compound of formula (V) is converted directly to the compound of formula (VII) by hydrogenolysis. The compound of formula (V) is dissolved in an inert solvent, preferably ethanol, and reacted with hydrogen at a pressure of about 1-5 atmospheres, preferably about 1 atmosphere, in the presence of a catalyst such as copper chromite, platinum on carbon or preferably palladium on carbon. The reaction is conducted at a temperature of about 0°-50° C., preferably about 25° C., until about 1 molar equivalent of hydrogen is absorbed, typically in about 2 hours. When the reaction is substantially complete, the product of formula (VII) is isolated by conventional means.

Alternatively, the compound of formula (VII) is obtained from the compound of formula (V) by reaction with about 1 to 4 molar equivalents, preferably about 2 molar equivalents, of sodium borohydride in anhydrous trifluoroacetic acid as a solvent. The reaction is conducted at a temperature of 0°-60° C., preferably about 25° C., for about 30 min. to 8 hours, preferably about 1 hour.

The compound of formula (VII) is then hydrolyzed to the compound of formula (VIII). Typically, the ketal of formula (VII) is stirred with a large excess of an inorganic acid, preferably about 6N hydrochloric acid, at a temperature of 0° C. to 50° C., preferably about 25° C., for about 30 minutes to 10 hours, preferably about 2 hours. When the reaction is substantially complete, the product of formula (VIII), 2-(3-pyridylmethyl)-6-acetylnaphthalene, is isolated by conventional means, for example chromatography.

The compound of formula (VIII) is then converted to the compound of formula (I) via the haloform reaction. Typically, about 3 to 10 molar equivalents, preferably about 5 molar equivalents, of bromine is added to a solution of about 10 to 50 molar equivalents, preferably about 18 molar equivalents, of an inorganic base, preferably sodium hydroxide, in water. The solution is maintained at about room temperature and the ketone of formula (VIII), dissolved in a water-miscible solvent, preferably tetrahydrofuran, is added. The mixture is stirred for about 30 minutes at ambient temperature, then refluxed for about 1 hour to 10 hours, preferably about 3 hours. When the reaction is substantially complete, the product of formula (I), 2-(3-pyridylmethyl)-naphthalene-6-carboxylic acid, is isolated by conventional means, for example crystallization.

The pharmaceutically acceptable basic non-toxic salt derivatives of the compound of formula (I) are prepared by treating the free acid with an appropriate amount of pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoethanol, lysine, arginine, histidine, procaine, choline, betaine, ethylenediamine, glucosamine, methylglucamine, theobromine, purines, piperazine, piperidine, N-ethylpiperidine, polyamine resins and the like. For preparing, for example, monovalent cation salts, the free acid starting material of formula (I) is treated with one molar equivalent of pharmaceutically acceptable base in an appropriate solvent such as water, methanol, ethanol, isopropanol, butanol, acetone, dioxane or tetrahydrofuran. The molar ratio of the compound of formula (I) to base used is chosen to provide the ratio desired for any particular salt. For preparing, for example, divalent cation salts such as the calcium or magnesium salts the free acid starting material of formula (I) is treated with at least one-half molar equivalent of pharmaceutically acceptable base to yield a neutral salt. Similarly, for the trivalent cation aluminum salts, at least one-third molar equivalent of the aluminum base is employed if a neutral salt product is desired.

The free carboxylic acid (I) can be reliberated from the respective salts by treating said salts with a stoichiometric quantity of a strong acid, preferably an inorganic acid, e.g., hydrochloric acid, sulfuric acid, and the like, at temperatures ranging from about 0° C. to about 50° C., preferably at room temperature.

The pharmaceutically acceptable non-toxic esters are formed with alkanols, optionally substituted benzyl alcohols or optionally substituted phenols. The pharmaceutically acceptable non-toxic esters of the carboxylic acid (I) can be prepared, e.g. by esterifying the corresponding free acid with a solution of the appropriate diazoalkane in a suitable inert solvent such as diethyl ether. An alternative and general method for producing the esterified acid of our invention comprises esterifying the corresponding free acid with an appropriate alcohol or phenol in the presence of a sufficient amount of an acid catalyst or, alternatively, a dehydrating agent, for example 1,3-dicyclohexylcarbodiimide, or a triphenylphosphine and a dialkylazodicarboxylate. Another method comprises reaction of a benzene solution of the carboxylic acid with an alkyl halide in the presence of the organic base diazabicycloundecane (DBU) at temperatures from about 20° C.-80° C., and for about 1-12 hours. (N. Ono et al, *Bull. Chem. Soc. Japan*, 51, 2401-2404 (1978)).

Typical esters are those esters derived from methyl alcohol, ethyl alcohol, propyl alcohol, isopropyl alcohol, butyl alcohol, 2-butyl alcohol, 2-pentyl alcohol, isopentyl alcohol, 2-hexyl alcohol, benzyl alcohol, phenol and the like.

Alternatively, the alkyl esters can be prepared by transesterification, catalyzed by the corresponding alkoxide according to methods known in the art. It is preferred in preparing the esters via transesterification to go from a lower ester to a higher ester, e.g., from the methyl ester to the isoamyl ester. However, by using a substantial excess of a lower alcohol, a higher ester can be transesterified to a lower ester; thus, for example, by using a substantial excess of ethanol, the hexyl ester is converted by transesterification to the ethyl ester.

The compound of formula I in free base form may be converted to acid addition salts by treating with a stoichiometric excess of the appropriate organic or inorganic acid, such as, for example, oxalic, citric, malonic, (±)-tartaric, (±)-lactic, phosphoric, hydrochloric or sulfuric acid and the like. Typically, the free base is dissolved in a polar organic solvent such as ethanol or methanol, and the acid added thereto. The temperature is maintained between about 0° C. and 50° C. The resulting acid addition salt precipitates spontaneously or may be brought out of solution with a less polar solvent.

The acid addition salts of the compound of formula I may be decomposed to the corresponding free base by treating with a stoichiometric amount of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Salts of the compound of formula (I) may be interchanged by taking advantage of differential solubilities of the salts volatilities or activities of the acids, or by treating with the appropriately loaded ion exchange resin. For example, the interchange is effected by the reaction of a salt of the compound of formula (I) with a slight stoichiometric excess of an acid of a lower pKa than the acid component of the starting salt. This conversion is carried out at a temperature between about 0° C. and the boiling point of the solvent being used as the medium for the procedure.

UTILITY AND ADMINISTRATION

The compounds of formula I have been shown in standard laboratory tests to be useful in treating diseases characterized by elevated thromboxane levels or an imbalance of prostacyclin/thromboxane in mammals. Accordingly, the compounds of formula I, their salts and esters and pharmaceutical compositions containing them, may be used in treating such disease states in mammals by administering a therapeutically effective amount of a compound of formula I to a mammal in need of such a treatment. The inhibition of thromboxane synthesis was determined by measurement of the ability to inhibit human platelet aggregation by ADP in standard tests as described by Example 12 below.

The amount of active compound administered will, of course, depend on the subject being treated, the severity of the affliction, the manner of administration and the judgment of the prescribing physician. However, a therapeutically effective dosage of compounds of the instant invention is in the range of 1–100 mg/kg/day, preferably about 2–50 mg/kg/day, and most preferably about 10 mg/kg/day. For an average 70 kg human, this would amount to 70 mg–7 g per day, or preferably about 700 mg/day.

Administration of the active compounds and salts described herein may be effected via any medically accepted mode of administration for agents which control thromboxane synthesis, platelet aggregation or associated activities.

These methods include but are not limited to oral, parenteral, topical and otherwise systemic routes of administration. Oral administration is preferred, depending of course, on the disorder being treated. The compounds are administered in a therapeutically effective amount either alone or in combination with a suitable pharmaceutically acceptable excipient.

Depending on the intended mode of administration, the compounds of this invention may be incorporated in any pharmaceutically acceptable dosage form, such as, for example, tablets, suppositories, pills, capsules, powders, liquids, suspensions, emulsions, aerosols, or the like. Preferable means of administration are unit dosage forms suitable for single administration of precise dosages, or sustained release dosage forms for continuous administration. Preferably the dosage form will include a pharmaceutically acceptable excipient and an active compound of formula I, or a pharmaceutically acceptable salt thereof, and, in addition, may include other medicinal agents, pharmaceutical agents, carriers, excipients, adjuvants, stabilizers, etc. Depending on parameters such as mode of administration, type of composition, and activity of the compound, the pharmaceutical composition may contain 1–95 percent by weight active ingredient, preferably 25–70 percent, with the remainder being excipient.

For solid dosage forms, non-toxic solid carriers include but are not limited to, for example, pharmaceutical grades of mannitol, lactose, starch, magnesium stearate, sodium saccharin, the polyalkylene glycols, talcum, cellulose, glucose, sucrose, and magnesium carbonate. An example of a solid dosage form of the compounds of this invention is a suppository containing propylene glycol as the carrier. Liquid pharmaceutically administerable dosage forms can, for example, comprise a solution or suspension of an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents the like. Typical examples of such auxiliary agents are sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.5%–10%; preferably 1–2%.

For oral administration, a pharmaceutically acceptable non-toxic dosage form may contain any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such dosage forms may contain 1%–95% active ingredient, preferably 25–70%.

The following Preparations and Examples serve to illustrate the invention and make the invention enabling. They should not be construed as narrowing it or limiting its scope in any way.

PREPARATION 1

Preparation of 2-bromo-6-acetylnaphthalene

A mixture of 41.4 g of 2-bromonaphthalene, 15.7 g of acetyl chloride and 28 g of aluminum chloride in 250 ml of nitrobenzene was stirred at 100° C. for 4 hours. The reaction mixture was poured onto ice water and the resulting solid filtered off, washed with water and distilled under reduced pressure. The distillate was recrystallized from hexane to yield 2-bromo-6-acetylnaphthalene.

PREPARATION 2

Preparation of 2-bromo-6-(2-methyl-1,3-dioxolan-2-yl)naphthalene.

A mixture of 13.0 g of 2-bromo-6-acetylnaphthalene, 20 g of ethylene glycol, 200 ml of benzene, and 530 mg of p-toluenesulfonic acid was heated at reflux for 18 hours using a Dean-Stark trap to effect continuous removal of water. The cooled reaction mixture was added to 100 ml of 0.1N sodium hydroxide solution and the resulting mixture extracted with three 75 ml portions of diethyl ether. The combined organic extract was washed with 100 ml saturated sodium chloride solution and then dried over sodium sulfate. The solvent is removed under vacuum and the residue recrystallized from hexane to give 12.2 g of 2-bromo-6-(2-methyl-1,3-dioxolan-2-yl)naphthalene, m.p. 80°–82° C.

PREPARATION 3

Preparation of 2-[(3-pyridyl)hydroxymethyl]-6-(2-methyl-1,3-dioxolan-2-yl)naphthalene A solution of 4.5 g of 2-bromo-6-(2-methyl-1,3-dioxolan-2-yl)naphthalene in 30 ml of tetrahydrofuran was cooled to −78° C. under nitrogen, and 14.0 ml of 2.2M t-butyl lithium added dropwise. A solution of 1.64 g of 3-pyridinecarboxaldehyde in 15 ml of tetrahydrofuran was added over a period of 10 minutes, and the temperature was allowed to rise to −20° C. during the next 30 minutes. The reaction was quenched with 30 ml of water and the mixture extracted with methylene chloride. The organic layer was dried over sodium sulfate and solvent removed under reduced pressure to give a solid that was recrystallized from methylene chloride/diethyl ether to give 3.1 g of 2-[(3-pyridyl)hydroxymethyl]-6-(2-methyl-1,3-dioxolan-2-yl)naphthalene, m.p. 154°–156° C.

PREPARATION 4

Preparation of 2-(3-pyridylcarbonyl)-6-(2-methyl-1,3-dioxolan-2-yl)naphthalene

A solution of 165 mg of oxalyl chloride in 20 ml of methylene chloride was cooled to −50° C., 203 mg of dimethylsulfoxide added dropwise, and the mixture stirred for 5 minutes. A solution of 321 mg of 2-[(3-pyridyl)hydroxymethyl]-6-(2-methyl-1,3-dioxolan-2-yl)naphthalene in 10 ml of methylene chloride was then added dropwise and the mixture stirred at −50° C. for 15 minutes. Triethylamine (506 mg) was added at −50° C. and the mixture stirred for 5 minutes, then allowed to warm to room temperature. The solution was washed with water, dried over sodium sulfate and the solvent removed under reduced pressure to give 300 mg of 2-(3-pyridylcarbonyl)-6-(2-methyl-1,3-dioxolan-2-yl)naphthalene as an oil.

PREPARATION 5

Preparation of 2-(3-pyridylmethyl)-6-(2-methyl-1,3-dioxolan-2-yl)naphthalene

A mixture of 270 mg of 2-(3-pyridylcarbonyl)-6-(2-methyl-1,3-dioxolan-2-yl)naphthalene, 7 ml of triethylene glycol, 1 ml of anhydrous hydrazine and 500 mg of potassium hydroxide were heated at 160° C. for 30 minutes. The temperature was then raised to 210° C. for 1 hour. The mixture was cooled, poured into water and extracted with methylene chloride. The organic layer was dried over sodium sulfate, the solvent removed under reduced pressure and the residue chromatographed on silica gel to give 160 mg of 2-(3-pyridylmethyl)-6-(2-methyl-1,3dioxolan-2-yl)naphthalene as an oil.

PREPARATION 6

Preparation of 2-(3-pyridylmethyl)-6-acetylnaphthalene

A solution of 150 mg of 2-(3-pyridylmethyl)-6-(2-methyl-1,3-dioxolan-2-yl)naphthalene in 15 ml of 1N hydrochloric acid was allowed to stand for 3 hours at room temperature. The solution was neutralized with sodium carbonate and extracted with methylene chloride. The organic layer was dried over sodium sulfate and the solvent removed under reduced pressure to give 130 mg of 2-(3-pyridylmethyl)-6-acetylnaphthalene as an oil.

EXAMPLE 1

Preparation of 2-(3-pyridylmethyl)naphthalene-6-carboxylic acid

To a solution of 700 mg of sodium hydroxide in 3.5 ml of water was added 780 mg of bromine. The mixture was cooled to room temperature and a solution of 260 mg of 2-(3-pyridylmethyl)-6-acetylnaphthalene in 2.5 ml of tetrahydrofuran added. The solution was stirred at room temperature for 45 minutes, then refluxed for 3 hours. The mixture was cooled to room temperature and 500 mg of sodium bisulfite added, followed by sufficient saturated sodium carbonate to bring the pH to about 14. The mixture was extracted with methylene chloride. The aqueous layer was then loaded onto a column with a 200 ml bed of Amberlite XAD-2 resin. The column was eluted with 300 ml of water, then water/ethanol mixture with a gradually increasing proportion of ethanol until elution with 100% ethanol occurred. The product was obtained as the sodium salt. Recrystallization from acetic acid/water mixture gave 2-(3-pyridylmethyl)naphthalene-6-carboxylic acid, which was purified via the methyl ester to its hydrochloride salt as shown below in Examples 2 and 3.

EXAMPLE 2

Preparation of methyl 2-(3-pyridylmethyl)naphthalene-6-carboxylate hydrochloride To a suspension of 350 mg of 2-(3-pyridylmethyl)naphthalene-6-carboxylic acid in 50 ml of ethyl acetate was added excess ethereal diazomethane, and the mixture stirred at room temperature for 1 hour. A few drops of acetic acid was added and the solution extracted with aqueous saturated sodium carbonate. The organic layer was dried over sodium sulfate and the solvent removed under reduced pressure to give methyl 2-(3-pyridylmethyl)naphthalene-B 6-carboxylate. The product was dissolved in diethyl ether and anhydrous hydrochloric acid in ether added with stirring. The precipitated salt was filtered off and dried under vacuum to give methyl 2-(3-pyridylmethyl)naphthalene-6-carboxylate hydrochloride, m.p. 187°–193° C.

EXAMPLE 3

Preparation of 2-(3-pyridylmethyl)naphthalene-6-carboxylic acid hydrochloride

A solution of 205 mg of methyl 2-(3-pyridylmethyl)-naphthalene-6-carboxylate hydrochloride in 15 ml of 6N hydrochloric acid was refluxed for 18 hours. The solution was cooled to room temperature and the precipitate filtered off, washed with cold 6N hydrochloric acid followed by acetone and air dried to give 2-(3-pyridylmethyl)naphthalene-6-carboxylic acid hydrochloride, m.p. 265°–270° C.

EXAMPLE 4

Preparation of 2-(3-pyridylmethyl)naphthalene-6-carboxylic acid from the hydrochloride salt A suspension of 2-(3-pyridylmethyl)naphthalene-6-carboxylic acid hydrochloride in 100 ml of methylene chloride is stirred with a stoichiometric amount of dilute aqueous sodium hydroxide solution until the salt is completely dissolved. The organic layer is separated, washed with water, dried over magnesium sulfate and evaporated to yield 2-(3-pyridylmethyl)naphthalene-6-carboxylic acid.

EXAMPLE 5

Preparation of sodium 2-(3-pyridylmethyl)naphthalene-6-carboxylate 2-(3-pyridylmethyl)naphthalene-6-carboxylic acid is dissolved in methanol and to this solution a stoichiometric amount of sodium bicarbonate dissolved in water is added. The mixture is stirred at room temperature for one hour, azeotroped with benzene twice and dried under high vacuum for 3 hours. The solid material is recrystallized from methanol and diethyl ether mixture and dried in vacuum at room temperature overnight to give sodium 2-(3-pyridylmethyl)naphthalene-6-carboxylate.

EXAMPLE 6

Platelet Aggregation Inhibition

Comparison of 2-(3-pyridylmethyl)naphthalene-6-carboxylic acid and 2-(3-pyridylmethyl)naphthalene-7-carboxylic acid.

1. 2-(3-pyridylmethyl)naphthalene-6-carboxylic acid
   Platelet Aggregation Inducer: ADP
   Concentration: $5 \times 10^{-6}$M

| Solvent | Concentration | % Inhibition | IC$_{50}$ |
|---|---|---|---|
| Water | $5 \times 10^{-4}$M | 87.3 | $1.6 \times 10^{-7}$M |
|  | $1 \times 10^{-4}$M | 85.2 |  |
|  | $2 \times 10^{-5}$M | 90.9 ± 1.3 |  |
|  | $5 \times 10^{-6}$M | 88.7 ± 3.5 |  |
|  | $1 \times 10^{-6}$M | 83.8 ± 4.0 |  |
|  | $2 \times 10^{-7}$M | 58.7 ± 9.2 |  |
|  | $5 \times 10^{-8}$M | 12.7 ± 0.7 |  |

-continued

| Solvent | Concentration | % Inhibition | IC$_{50}$ |
|---|---|---|---|
| Water | $1.0 \times 10^{-6}$M |  | $7.9 \times 10^{-8}$M |
|  | $2.0 \times 10^{-7}$M |  |  |
|  | $1.0 \times 10^{-7}$M |  |  |
|  | $5.0 \times 10^{-8}$M |  |  |
| Water | $5.0 \times 10^{-4}$M | 96.6 | $1.7 \times 10^{-6}$M |
|  | $1.0 \times 10^{-4}$M | 98.3 |  |
|  | $2.0 \times 10^{-5}$M | 97.4 ± 1.3 |  |
|  | $5.0 \times 10^{-6}$M | 96.6 ± 0.1 |  |
|  | $1.0 \times 10^{-6}$M | 13.7 ± 4.4 |  |
| Water | $5.0 \times 10^{-6}$M | 100.0 | $6.0 \times 10^{-8}$M |
|  | $1.0 \times 10^{-6}$M | 100.0 |  |
|  | $2.0 \times 10^{-7}$M | 97.1 ± 1.9 |  |
|  | $5.0 \times 10^{-8}$M | 37.8 ± 40.1 |  |
|  | $2.0 \times 10^{-8}$M | 1.6 |  |
| Water | $5.0 \times 10^{-5}$M | 86.8 ± 1.8 | $1.15 \times 10^{-7}$M |
|  | $5.0 \times 10^{-6}$M | 85.1 ± 4.1 |  |
|  | $5.0 \times 10^{-7}$M | 78.3 |  |
|  | $1.0 \times 10^{-7}$M | 47.0 ± 5.2 |  |
|  | $5.0 \times 10^{-8}$M | 18.7 ± 4.3 |  |
| Water | $5.0 \times 10^{-5}$M | 86.5 ± 2.2 | $1.8 \times 10^{-7}$M |
|  | $5.0 \times 10^{-6}$M | 85.3 ± 5.5 |  |
|  | $5.0 \times 10^{-7}$M | 75.8 ± 3.5 |  |
|  | $1.0 \times 10^{-7}$M | 29.3 ± 3.7 |  |
|  | $5.0 \times 10^{-8}$M | 17.6 ± 3.0 |  |
|  | $1.0 \times 10^{-8}$M | 4.7 |  |

2. 2-(3-pyridylmethyl)naphthalene-7-carboxylic acid

| Solvent | Concentration | % Inhibition | IC$_{50}$ |
|---|---|---|---|
| Water | $5.0 \times 10^{-4}$M | 92.8 | $2.1 \times 10^{-5}$M |
|  | $1.0 \times 10^{-4}$M | 88.8 |  |
|  | $2.0 \times 10^{-5}$M | 47.9 |  |
|  | $5.0 \times 10^{-6}$M | 18.2 |  |

EXAMPLES 7–11

In examples 7 through 11 the active ingredient is 2-(3-pyridylmethyl)naphthalene-6-carboxylic acid. However, other pharmaceutically acceptable acid or base salts thereof may be substituted therein.

EXAMPLE 7

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 8

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 9

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 10

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 11

A solution preparation buffered to a pH of 7 is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water q.s. to | 100 ml |

EXAMPLE 12

Determination of Inhibition and Thromboxane Synthetase Activity Utilizing Human Platelet Aggregation Human platelet-rich plasma preparation:

Blood sample is collected into siliconized vacutainers containing sodium citrate (0.5 ml of 11.25% sodium citrate per 15 ml vacutainer) final concentration 0.38%. Platelet rich plasma (PRP) is obtained after centrifuging the blood for 15 minutes at 200 xg at room temperature. Blood and plasma contacts only non-wettable plastic or siliconized glass surfaces. Procedure:

1. Aggregation is followed by the turbidimetric method of Born (*J. Physiol.* 162, 67p, 1962), using a Payton Dual Channel Aggregometer.

2. PRP-PAM control. 1.0 ml PRP is used. Pig aortic microsomes (PAM), prepared according to Neichi, et al. (*Prostaglandins*, 19(4), 577–86 (1980)), are incubated in PRP at 37° C. with stirring for 3 minutes, immediately followed by addition of inducer-ADP. The concentration of PAM is chosen to show little or no inhibition of platelet aggregation when compared with the aggregation of PRP alone.

3. PRP-PAM plus thromboxane synthetase inhibitor.

Thromboxane synthetase inhibitor is added to 1.0 ml PRP incubated at 37° C. with stirring for two minutes. The PAM concentration is chosen according to step 2, and is added to PRP incubated at 37° C. with stirring for another 3 minutes. The inducer ADP is added immediately afterwards.

What is claimed is:

1. A method of inhibiting thromboxane synthetase in a mammal having a disease characterized by elevated thromboxane levels or an imbalance of prostacyclin/-thromboxane levels which method comprises:

administering to a mammal in need of such a treatment a therapeutically effective amount of a compound of the formula

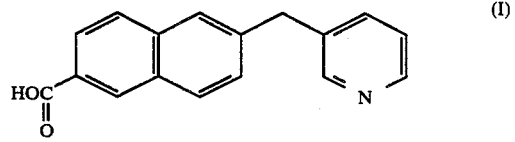

(I)

or a pharmaceutically acceptable salt or ester thereof, wherein the ester is derived from a lower alcohol, benzyl alcohol, or phenol.

2. A pharmaceutical composition suitable for administration to a mammal having a disease-state which is alleviated by treatment with a thromboxane synthetase inhibitor which comprises a therapeutically effective amount of a compound of formula (I), or a pharmaceutically acceptable salt or ester thereof, wherein the ester is derived from a lower alcohol, benzyl alcohol, or phenol, in admixture with one or more pharmaceutically acceptable excipients.

3. A compound of the formula

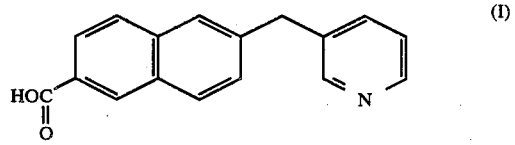

(I)

or a pharmaceutically acceptable salt or ester thereof, wherein the ester is derived from a lower alcohol, benzyl alcohol, or phenol.

* * * * *